(12) United States Patent
Dunne (10) Patent No.: US 8,714,151 B2
(45) Date of Patent: May 6, 2014

(54) ATOMIZING DEVICE, INHALER AND METHOD FOR DISPENSING A LIQUID FORMULATION

(75) Inventor: Stephen T. Dunne, Stowmarket (GB)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 504 days.

(21) Appl. No.: 12/812,624

(22) PCT Filed: Jan. 16, 2009

(86) PCT No.: PCT/EP2009/000251
§ 371 (c)(1),
(2), (4) Date: Aug. 25, 2010

(87) PCT Pub. No.: WO2009/090083
PCT Pub. Date: Jul. 23, 2009

(65) Prior Publication Data
US 2011/0041840 A1    Feb. 24, 2011

(30) Foreign Application Priority Data
Jan. 16, 2008 (GB) .................................. 0800708.0

(51) Int. Cl.
*A61M 15/00* (2006.01)
*A61M 16/00* (2006.01)
*A61M 11/00* (2006.01)

(52) U.S. Cl.
USPC ................................. 128/203.21; 128/200.14

(58) Field of Classification Search
USPC ............. 128/200.22, 200.14, 200.24, 203.12, 128/200.18, 203.15, 203.21; 604/58, 71, 72
See application file for complete search history.

(56) References Cited

U.S. PATENT DOCUMENTS

| | | | |
|---|---|---|---|
| 5,201,308 A * | 4/1993 | Newhouse | 128/203.15 |
| 5,511,538 A | 4/1996 | Haber et al. | |
| 6,889,687 B1 | 5/2005 | Olsson | |
| 7,147,132 B2 * | 12/2006 | Tabata et al. | 222/82 |
| 2003/0075623 A1 | 4/2003 | Bartels et al. | |
| 2007/0163574 A1 * | 7/2007 | Rohrschneider et al. | 128/200.19 |

FOREIGN PATENT DOCUMENTS

| | | |
|---|---|---|
| CA | 2644013 A1 | 10/2007 |
| EP | 0308100 A1 | 3/1989 |
| WO | 0117595 A1 | 3/2001 |
| WO | 0213886 A2 | 2/2002 |
| WO | 03061844 A1 | 7/2003 |

OTHER PUBLICATIONS

International Search Report for PCT/Ep2009/000251 mailed May 19, 2009.

* cited by examiner

*Primary Examiner* — Jackie Ho
*Assistant Examiner* — Ned T Heffner
(74) *Attorney, Agent, or Firm* — Michael P. Morris; David L. Kershner (57) ABSTRACT

An atomizing device (1), an inhaler and a method for dispensing a liquid formulation (5) are proposed. An insert (2) comprises a cylinder (4) filled with the liquid, an atomizing nozzle (7) and a piston (6). The piston is moved in the cylinder to pressurize the liquid and force it out of cylinder through the atomizing nozzle in order to generate a spray (13). The insert is received in a holder (3) which is sealed. The insert is moved within the holder so that the sealing (9) is ruptured before the spray is generated.

4 Claims, 5 Drawing Sheets

ATOMIZING DEVICE, INHALER AND METHOD FOR DISPENSING A LIQUID FORMULATION

The present invention relates to an atomizing device, an inhaler and a method for dispensing a liquid formulation containing or consisting of a drug or mixture of drugs.

The liquid formulation is preferably a medicament. The term "liquid" has to be understood preferably in a broad sense covering inter alia solutions, suspensions, suslutions (mixtures thereof) or the like.

More particularly, the present invention relates to the dispensing of formulations for inhalation, such as medical formulations containing or consisting of at least one drug.

The present invention is preferably concerned with inhalers for delivery of liquid formulations or drugs. In particular, the inhalers may comprise atomizing devices as described herein or may use methods for dispensing a liquid formulation as described herein.

Inhalers are subdivided into single dose and multi-dose devices or inhalers. Multi-dose inhalers are further subdivided into pre-metered types where the doses are stored individually and into metering inhalers where each dose is metered in the device.

The present invention relates in particular to so-called metered dose inhalers (or atomizing devices) where a single dose or multiple doses are pre-metered and stored individually. This pre-metering has the advantage that the single doses are metered under strict factory conditions.

The invention is concerned in particular with gas free-metered dose inhalers (or atomizing devices) for the delivery of liquid formulations or drugs to the lungs or nose.

U.S. Pat. No. 5,662,271 A describes a metered dose inhaler comprising a piston which is mounted in a cavity within a body, and is urged by a pre-loaded spring into a pressure chamber. The piston may be loaded by means of an actuating rod having a handle, and may be latched in a loaded position by latching means. A liquid drug is contained in a collapsible back. Metered quantities of the drug are subsequently delivered into the pressure chamber and, then, subjected to a sudden and great increase in pressure, to eject the liquid drug thorough an atomizing head in order generate a spray of small particles or droplets. Non-return valves control the flow of the liquid through the device. The sudden pressure increase is caused by releasing a spring loaded piston, upon releasing a latching means. In this inhaler, both the piston/cylinder and atomizing head are used many times to atomize each drug dose. This may lead to problems with contamination and/or metering tolerances.

Object of the present invention is to provide an atomizing device, an inhaler and a method for dispensing a liquid formulation containing or consisting of a drug or mixture of drugs, wherein high standards of exact pre-metering and/or individual sealing of doses can be met and/or where it is possible to unseal a dose of the liquid formulation in an easy manner and/or only just before atomization.

The above object is achieved by an atomizing device for a liquid drug or formulation containing or consisting of a drug, wherein the atomizing device comprises an insert and a holder for holding the insert, wherein the insert comprises a cylinder filled with the formulation, a piston and an atomizing means, the piston being moveable in the cylinder to pressurize the drug or formulation and force it out of the cylinder through the atomizing means in order to generate a spray of the drug or formulation, wherein the insert is sealed in the holder by means of a sealing, wherein the insert is moveable within the holder in order to rupture the sealing before the drug or formulation is forced out of the cylinder through the atomizing means in order to generate a spray of the drug or formulation, The above object is also achieved by an inhaler for dispensing a liquid formulation, containing or consisting of a drug, as a spray, wherein the inhaler comprises an atomizing device with multiple cylinders respectively filled with the formulation, wherein an atomizing means and a piston are associated to each cylinder, each piston being moveable in the cylinder to pressurize the formulation and force it out of the respective cylinder through the respective atomizing means in order to generate the spray of formulation.

The above object is also achieved by a method for dispensing a liquid formulation, containing or consisting of a drug, as a spray from an atomizing device which comprises an insert and a holder holding the insert, the insert being sealed in the holder bv means of a sealing, the insert comprising a cylinder filled with the formulation, an atomizing means and a piston, wherein the insert is moved relative lo the holder in order to rupture the sealing and, then, the piston is moved in the cylinder to pressurize the formulation and force it out of the cylinder through the atomizing means in order to generate the spray of the formulation.

The present invention is directed in particular to a single pre-metered dose piston/cylinder arrangement with an atomizing means or nozzle hermetically sealed within a holder. A number of these may be used together to form a multi dose inhaler or an atomizing device with multiple doses.

Preferably, the atomizing device or inhaler comprises:
a cylinder or insert filled with a liquid formulation or drug having at one end an atomizing means or nozzle and at the other a piston;
an insert holder for holding the insert being sealed at both ends with a sealing, in particular a barrier foil;
means for moving the insert within the holder from a rest position to an operating position and to push the piston towards the atomizing means thus pressurizing the liquid and forcing it out through the atomizing means.

More than one insert/holder may mounted on a carrier, such as a ring or flexible tape, to form a multi dose device.

The atomizing means or nozzle may be a double or multi jet impinging nozzle, a solid impactor, a swirl chamber nozzle, or any other mechanical break up nozzle.

A filter may be mounted stream-up or behind the atomizing means or nozzle although this may not be needed because the atomizing means or nozzle is used preferably only once.

The metered dose of liquid (each dose) is preferably between 2 and 50 µl. The liquid formulation or drug may be a solution, a suspension or a mixture of both.

One great advantage of the present invention is that the liquid is pre-metered. This eliminates the need for a storage container, such a collapse back or tube, with the attendant evaporation problems during storage and use. Unlike metering devices where the container can have 2 to 3 times the required amount of liquid, there is very little waist of drug as near to all of the drug is dispensed each time. Another advantage is that the atomizing means or nozzle can be a very simple construction as it is used only once and there is no need for return valves, filters and other expensive and troublesome components. Likewise cheap plastics may be used as the inserts or cylinders are subject only to one cycle unlike in a metering device such as that described in U.S. Pat. No. 5,662,271 A.

Further aspects, advantages and features of the present invention will be apparent from the claims and following detailed description of preferred embodiments. In the drawings it shows:

In the Fig., the same reference signs are used for same or similar components, wherein same or similar characteristics, features or advantages are or can be realized or achieved even if a repeated discussion is omitted. Further, the features and aspects of the different embodiments can be combined in any desired manner and/or used for other inhalers or methods for dispensing of in particular medical formulations for inhalation.

Figure 1:
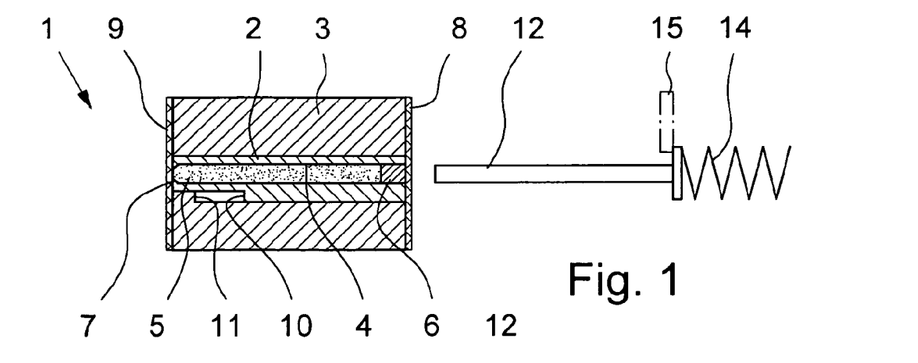
FIG. 1 a schematic sectional view of an atomizing device according to the present invention in a sealed state.
Figure 2:
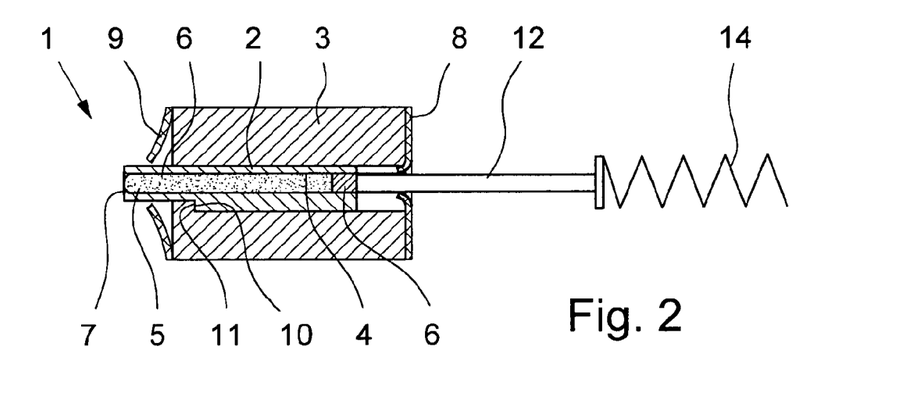
FIG. 2 a schematic sectional view of the atomizing device in an unseal state.
Figure 3:
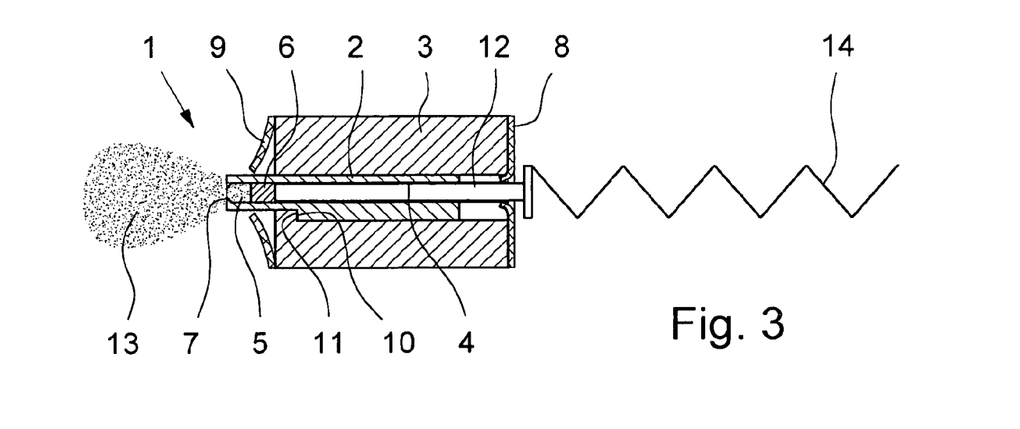
FIG. 3 a schematic sectional view of the atomizing device during dispensing.

FIGS. 1 to 3 show in a schematic sectional view—for illustration purposes not in scale—an atomizing device 1 according to the present invention. The atomizing device 1 comprises an insert 2 and an associated holder 3 for holding the insert 2. The insert 2 is received in the holder 3 in particular such that the insert 2 can be moved or shifted, preferably at least partially outwards of the holder 3.

The holder 3 holds a cylinder 4 filled with a metered dose or amount of a liquid 5 (i.e. a liquid formulation containing or consisting of a drug or a mixture of drugs). The cylinder 4 is preferably formed by the insert 2 or the cylinder 4 forms the insert 2. Preferably, the insert 2 contains the dose of liquid 5.

The insert 2 or cylinder 4 comprises a piston 6 moveable within the cylinder 4 for pressurizing and discharging the liquid 5 via an atomizing means 7, such as an atomizing duct or nozzle.

Preferably, the piston 6 is located at one end of the insert 2 or cylinder 4 (at least in its initial position before dispensing the liquid 5) and the atomizing means 7 at the other end. However, other constructional solutions are possible as well.

It has to be noted that the cylinder 4 is preferably cylindrical or circular in cross section. However, the cylinder 4 may have also any other suitable cross sectional form, e.g. may be rectangular in cross section. Thus, the term "cylinder" has to be understood preferably in a sufficiently broad sense.

FIG. 1 shows the atomizing device 1 or the insert 2 and piston 6 in a rest position or in a sealed state.

The insert 2 or holder 3 is hermetically sealed by sealings, preferably by foils 8 and 9, here at its open ends on opposite sides as schematically shown in FIG. 1. Preferably, the sealing or foil 8, 9 is only or mainly attached to the holder 3, but contacts or is biased against the insert 2 or cylinder 4 (at least at the outlet side or nozzle 7) in order to keep the liquid 5 in the insert 2/cylinder 4.

FIG. 2 shows in a similar sectional view the atomizing device 1 in a ready to fire or (first) operating position or activated position. The insert 2 has been pushed or moved so that the sealing or foil 9 is ruptured at the outlet side of the insert 2, cylinder 4 and/or atomizing means or nozzle 7 (at the left side in FIG. 2).

Preferably, the insert travel is limited. Preferably the insert 2 comprises a step or shoulder 10 cooperating with a stop or abutment 11 in the holder 3 to limit the travel of the insert 2 within the holder 3 or movement of the insert 2 partially outwardly of the holder 3. However, other constructional solutions are possible as well.

The insert 2 is preferably pushed or moved by a means, such an associated push rod 12, for moving the respective insert 2 within the holder 3 from the rest position to the operating or activated position and, thus, rupturing the respective sealing (here foil 9), i.e. for opening the outlet of the atomizing device 1 or insert 2 or atomizing means 7.

In the present embodiment, the means for moving the insert 2 (the push rod 12) perforates or pierces the (optional) sealing (foil 8) at the other end opposite of the outlet side as schematically shown in FIG. 2. The means may cooperate with or act directly on the insert 2 and/or cylinder 4 and/or piston 6. In the latter case, the means for moving the insert 2 forms preferably also a means to push the piston 6 towards the atomizing means to pressurize the liquid 5 and force it out through the atomizing means in a dispensing operation. Then, the friction between the piston 6 and the insert 2 or cylinder 4 and the force required to force the liquid 5 through the atomizing means 7 have to be greater than the friction and rupture force required to move the insert 2 within the holder 3 from the rest position shown in FIG. 1 into the operating or activated position shown in FIG. 2. Namely, the insert 2 shall be in the operating position (FIG. 2) before the piston 6 is moved within the insert 2 or cylinder 4 to pressurize and discharge the liquid 5.

FIG. 3 shows in a similar sectional view the atomizing device 1 during dispensing. In the dispensing operation, the piston 6 is pushed or moved by the respective means, here push rod 12, preferably all the way, to the insert end so that the liquid 5 is pressurized and discharged via the atomizing means 7 and, thus, atomized into an aerosol or spray 13 schematically shown in FIG. 3.

The means to move the insert 2 and/or the piston 6 within the insert 2 (here the push rod 12) is preferably spring loaded and/or driven by a spring 14 schematically shown in FIGS. 1 to 3. However, the means or push rod 12 may be powered or operated or driven by any other preferably mechanical means such as a gas spring or the like, but also by an electric motor or any hydraulic or pneumatic mechanism, such as an air compressor, pump or the like.

In the present embodiment, the movement of the insert 2 and the movement of the piston 6 (i.e. opening of the outlet and pressurizing and atomizing of the liquid 5) are performed immediately one after the other, i.e. without stop, preferably by the same or common means (here push rod 12). However, it is also possible to use different means and/or to stop inbetween, i.e. in the intermediate position in shown FIG. 2.

For a multi dose device (atomizing device 1 or inhaler 16) multiple holders 3 containing inserts 2 may be mounted on a carrier, such as a ring or flexible strip or the like, in particular 1 to 180. A respective embodiment of an inhaler 16 is shown in FIGS. 4 and 5 and will be explained later in more detail. All holders 3 can also be formed by the common carrier 17 or by a common holder 18. During use, a patient (not shown) can pull back the means to move the insert 2/piston 6, i.e. the push rod 12, in a retracted position, where the means, the push rod 12 or spring 14, is held by a latch 15 as schematically shown in FIG. 1. Preferably, during the retraction step, the holders 3/inserts 2 are indexed, i.e. the next holder 3/insert 2 is positioned before the push rod 12. Then, the atomizing device 1 or inhaler is ready for the next use or discharge.

When, the latch 15 is released, e.g. by means of a trigger button 19 (shown in FIG. 4) pushed by the patient, the spring 14 forces the push rod 12 into the holder 3/insert 2 first moving the insert 2 forward to the operating position and rupturing the outlet sealing or foil 9 (FIG. 2) and, then, forcing the piston 6 along the cylinder 4 to discharge the respective dose of liquid 5 as spray 13 (FIG. 3).

The piston 6 is adapted to the inner cross section of the cylinder 4, in particular such that an additional sealing between the piston 6 and the cylinder wall is not necessary.

The piston 6 is preferably made from a soft material, in particular plastic or rubber.

Figure 4:
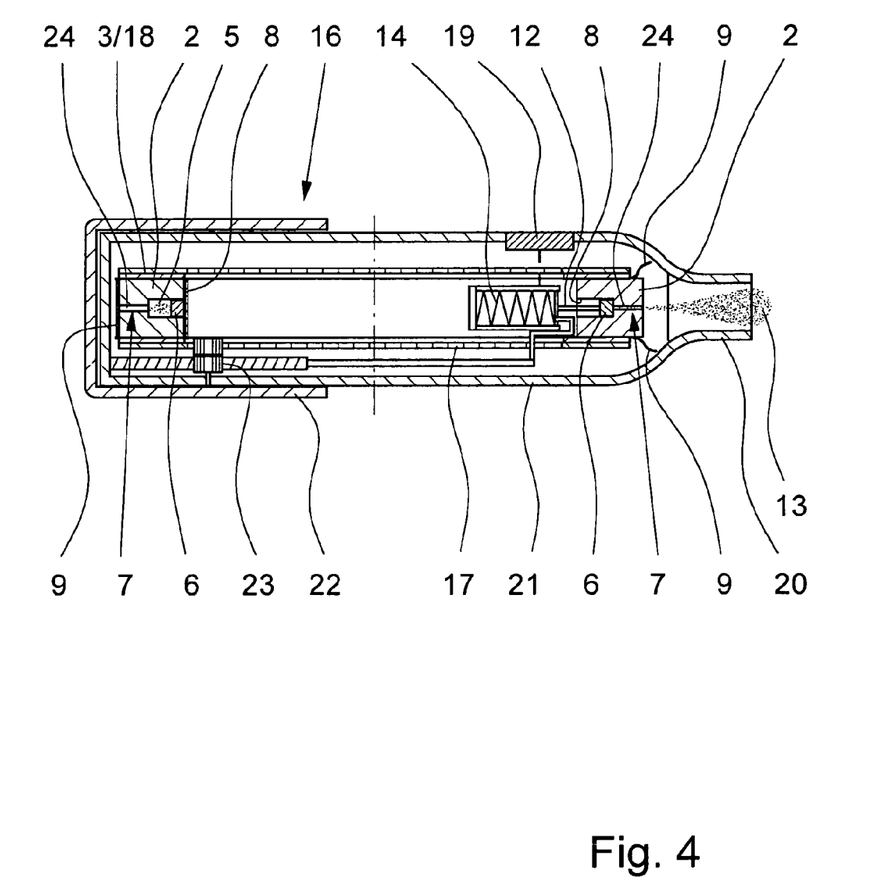
FIG. 4 a schematic sectional view of an inhaler according to the present invention with another atomizing device.

FIG. 4 shows in a very schematic sectional view the inhaler 16 according to the present invention. The inhaler 16 comprises in particular an atomizing device 1 as already described or as described in the following.

The inhaler 16 or atomizing device 1 comprises multiple cylinders 4 respectively filled with a pre-metered dose of liquid 5, i.e. the liquid formulation containing or consisting of a drug or a mixture of drugs. FIG. 4 shows on the left side a still filled cavity or cylinder 4 and on the right side an already emptied cavity or cylinder 4.

An atomizing means 7 and a piston 6 are associated to each cylinder 4. Each piston 6 is moveable in the cylinder 4 to pressurize the liquid 5 and force it out of the respective cylinder 4 through the respective atomizing means 7 in order to atomize the liquid 5 and generate the spray 13 as schematically shown in FIG. 4 on the right side.

In the shown embodiment, the inhaler 16 comprises a mouthpiece 20 or any other endpiece to discharge the spray 13.

In the shown embodiment, the cylinders 4 are preferably arranged annularly and/or one after the other e.g. in a row. However, other constructional solutions are possible.

Preferably, the cylinders 4 are formed by respective inserts 2 as already described with reference to FIGS. 1 to 3. Preferably, the inserts 2 are received or supported or held by multiple holders 3 arranged on the common carrier 17 or by a common holder 18 as schematically shown in the partial sectional view of one atomizing device 1 shown in FIG. 5. Here, the common holder 18 forms the ring-like carrier 17 for moveably holding the multiple inserts 2. However, other constructional solutions are possible as well.

Figure 5:
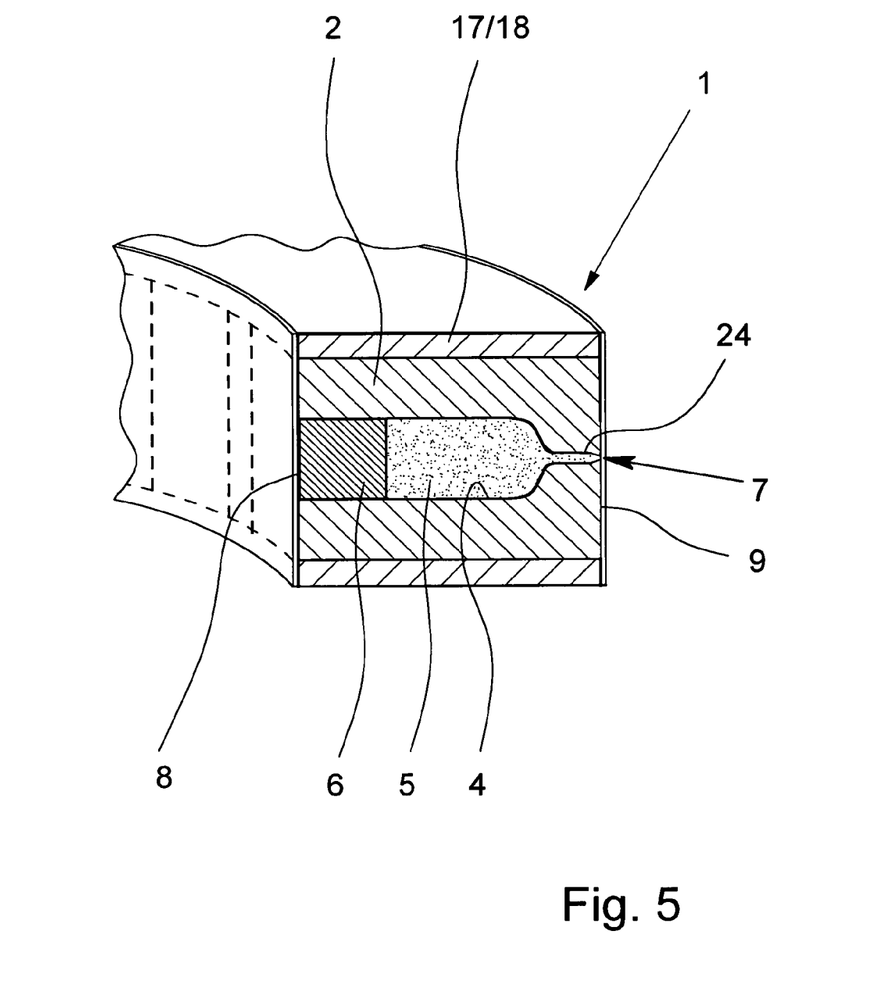
FIG. 5 a schematic sectional view of the atomizing device of the inhaler.

In the shown embodiment, the cylinders 4 or inserts 2 and/or holders 3 are preferably arranged in a ring and/or orientated radially. However, other configurations are possible as well.

The ring arrangement, carrier 17 and/or common holder 18 can be rotated in the embodiment according to FIG. 4 in order to index or move onwards to the next cylinder 4, insert 2 and/or holder 3. Thus, it is possible to align the filled cylinders 4/inserts 2 one after the other with the means to push the respective insert 2 outwards and/or the means to push the respective piston 6 towards the atomizing means 7 in order to pressurize the liquid 5 and force it out through the atomizing means 7.

The means to push the piston 6 are formed in the present embodiment preferably by the push rod 12. This forms together with its associated drive, here the spring 14 and latch 15, a discharge device of the inhaler 16.

The inhaler 16 comprises further preferably an opening device for individually opening the outlets of the cylinders 4 or atomizing means 7. This opening device is formed preferably by the means to move or push the inserts 2 individually outwards and or through the sealing (foil 9) covering the respective outlet. In the present case, the opening device and the discharge device even use the same or a common means, namely the push rod 12. However, other constructional or functional solutions are possible.

The inhaler 16 comprises preferably a housing 21 for receiving the cylinders 4, inserts 2, holders 3 and/or the carrier 17 or common holder 18 and/or the atomizing device 1.

The discharge device and/or opening device are preferably arranged within the housing 21 and/or the respective piston 6 and/or insert 2 and/or the push rod 12 run preferably in radial direction and/or in a main discharge direction and/or towards the mouthpiece 20 of the inhaler 16.

In the shown embodiment, the opening and discharge device of the inhaler 16 comprises the spring 14 driving the push rod 12 and the associated latch 15 (not in shown in FIG. 4).

Preferably, the inhaler 16 further comprises a release means, such as the button 19, which can be actuated or depressed by a patient (not shown) in order to release the spring 14 or any other energy store when discharge and atomizing of the respective dose of liquid 5 shall take place.

The operation of the inhaler 16 is preferably similar to the one described with reference to FIGS. 1 and 3. Then, the liquid 5 is discharged as spray 13 through the mouthpiece 20 as shown in FIG. 4 and can be inhaled by the patient.

The inhaler 16 comprises preferably an actuating means 22, such as a handle, cover or the like, to operate or drive the opening and/or discharge device, in particular to retract the push rod 12 and/or compress the spring 14. In the shown embodiment, the actuating means 22 can be pulled in order to retract the push rod 12 and to compress the spring 14 until it is latched to by latch 15 (not shown in FIG. 4). The actuating means 22 preferably drives also the atomizing device 1 or carrier 17 or common holder 18 such that the desired onward movement or indexing to the next cylinder 4/insert 2 is achieved. For this purpose a respective drive or transmission 23 such as a toothed rod, associated gears meshing with the rod and/or the carrier 17 or the like, and an appropriate freewheel or the like, may be provided.

In the following, some preferred aspects and features relating to the design of the cylinders 4, inserts 2 and atomizing means 7 are discussed.

The cylinder 4 may be formed as a through hole or bore with more or less constant diameter as schematically shown in FIG. 1 to 3.

Preferably, the length of the cylinder 4 or of the travel of piston 6 is greater, in particular at least by the factor 5 or 10, than the diameter of piston 6.

In the embodiment shown in FIGS. 1 to 3, the atomizing means 7 may be formed by a nozzle with reduced diameter and/or multiple nozzle openings. In particular, a respective nozzle member could be inserted into the insert 2 or the end of cylinder 4.

Figure 6:
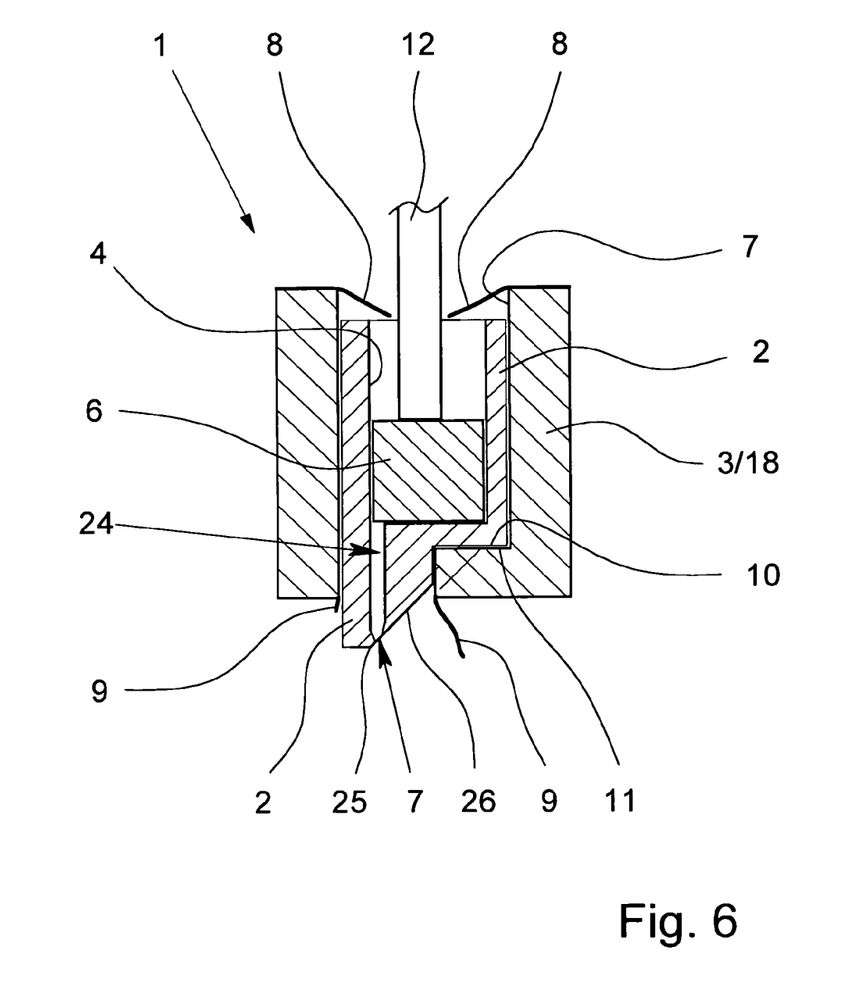
FIG. 6 a schematic sectional view of an insert of another atomizing device.

However, the atomizing means 7 can be formed alternatively only by a straight duct, e.g. by the cylinder 4 itself, or by a duct 24 with smaller diameter than cylinder 4 as shown in FIGS. 4, 5 and 6.

FIG. 6 shows in a very schematic sectional view a further embodiment of the atomizing device 1 or an insert/holder/piston arrangement according to the present invention in a state similar to the one shown in FIG. 3. The insert 2 comprises a cutting edge 25 and/or an inclined portion 26 at its outlet side or end with the atomizing means 7 (duct 24) to facilitate breaking of the sealing or foil 9 or to ensure a defined breaking or opening of sealing or foil 9.

Figure 7:
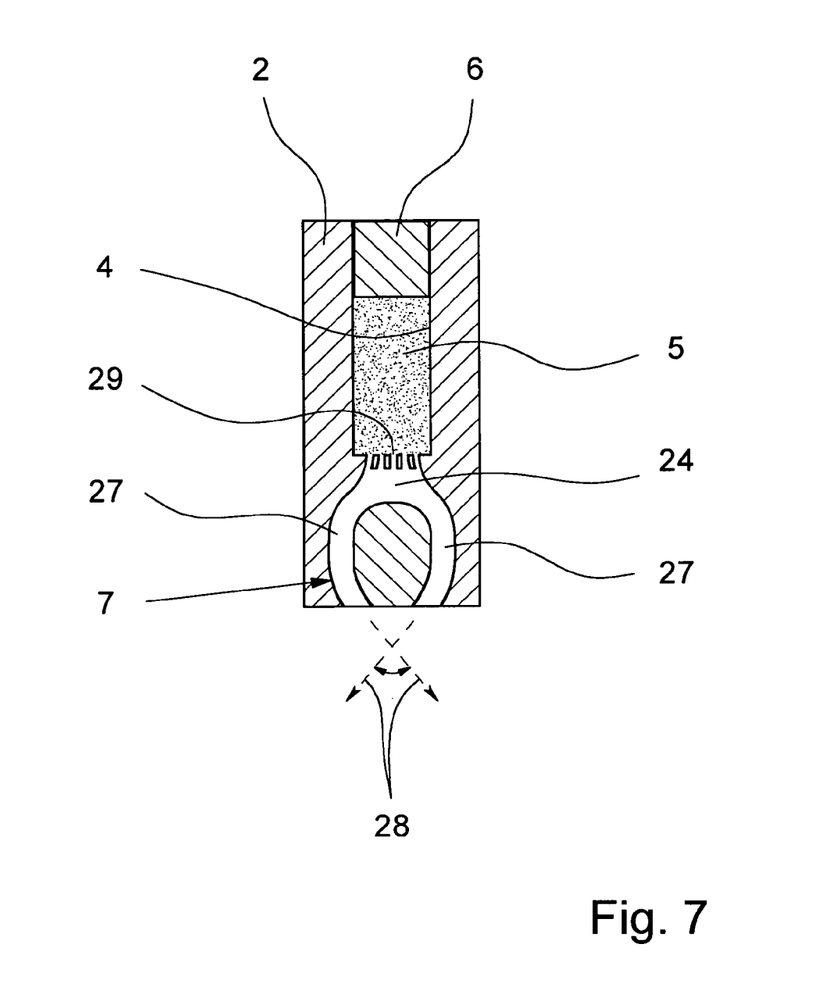
FIG. 7 a schematic sectional view of a further atomizing device or insert.

FIG. 7 shows in a sectional view an insert 2 (without holder 3 and without sealings) according to a further embodiment. Here, the atomizing means 7 forms or comprises a jet impinging means (double jet impinging nozzle or mechanic break up nozzle). The cylinder 4 or subsequent duct 24 splits up into at least two flow paths 27 to generate two jets 28 (shown by dashed arrows) of the liquid 5 during dispensing. The jets 28 intersect each other in a distance from the insert 2 in order to slow down the discharge speed and/or to support forming of a very fine spray 13 (not shown in FIG. 7).

The atomizing means 7 may also be designed as shown in US 2003/0075623 A1, if desired without a filter.

Preferably, the insert 2, holder 3 and/or atomizing means 7 are made of plastic, ceramic, glass, metal, or silicon. The atomizing means 7 are preferably made of silicon, glass, metal, in particular stainless steel, or ceramic.

Optionally, a filter 29 can be provided between the cylinder 4 and the atomizing means 7 as schematically shown in FIG. 7.

Preferably, each cylinder 4 contains a metered dose volume of the liquid 5, each dose being preferably between 1 and 100 μl.

Preferably, the pressure generated within the cylinder 4 is between 5 and 60 MPa.

Preferably, the particles or droplets generated by the atomizing means 7, i.e. the particles or droplets of the spray 13, have a mean mass diameter of between 2 and 8 micrometers.

The atomizing device 1 or inhaler 16 may comprise a magazine (reservoir) with multiple inserts 2 and holders 3.

Preferably, the force to push the insert 2 and/or piston 6, in particular the spring force, is between 5 N and 80 N, in particular between 10 N and 60 N.

The present invention also relates to a method for dispensing a liquid 5, e.g. a medical formulation, containing or consisting of a drug or mixture of drugs, as spray 13 from an atomizing device 1 which comprises an insert 2 and a holder 3 holding the insert 2. The insert 2 is sealed in the holder 3 by means of a sealing. The insert 2 comprises a cylinder 4 filled with the liquid 5, an atomizing means 7 and a piston 6. The insert 2 is moved relative to the holder 3 in order to rupture the sealing and, then, the piston 6 is moved in the cylinder 4 to pressurize the liquid 5 and force it out of the cylinder 4 thorough the atomizing means 7 in order to generate the spray 13 of the liquid 5.

In particular, the same means, such as push rod 12, is used to move the insert 2 and, then, the piston 6.

According to another aspect of the present invention which could be realized also independently, a common means, such as the push rod 12, is used for an atomizing device 1 which comprises multiple doses of liquid 5 in separate cavities or cylinders 4. The means is used to individually open the cavities or cylinders 4 or associated atomizing means 7 and, then, pressurize and discharge the doses of liquid 5 individually through the respective atomizing means 7. A further aspect is that all this is done by one common and/or linear movement.

Preferably, an atomizing device, an inhaler and a method for dispensing a liquid formulation are proposed. An insert comprises a cylinder filled with the liquid, an atomizing nozzle and a piston. The piston is moveable in the cylinder to pressurize the liquid and force it out of cylinder through the atomizing nozzle in order to generate a spray. The insert is received in a holder which is sealed. The insert is moveable within the holder so that the sealing can be ruptured before the spray is generated.

LIST OF REFERENCE NUMBERS 1 atomizing device
2 insert
3 holder
4 cylinder
5 liquid
6 piston
7 atomizing means
8 foil
9 foil
10 shoulder
11 abutment
12 push rod
13 spray
14 spring
15 latch
16 inhaler
17 carrier
18 common holder
19 button
20 mouthpiece
21 housing
22 actuating means
23 transmission
24 duct
25 cutting edge
26 inclined portion
27 flow path
28 jet
29 filter

The invention claimed is:

1. Inhaler (16) for dispensing a liquid formulation containing a drug as a spray (13), wherein the inhaler (16) comprises an atomizing device (1) with multiple cylinders (4) respectively filled with the formulation, wherein an atomizing means (7) and a piston (6) are associated to each cylinder (4), each piston (6) being moveable in the cylinder (4) to pressurize the formulation and force it out of the respective cylinder (4) through the respective atomizing means (7) in order to generate the spray (13) of formulation;
    wherein
    the inhaler (16) or atomizing device (1) comprises multiple inserts (2) and holders (3), each insert (2) forming one of the cylinders (4) and comprising the respective atomizing means (7), each insert (2) being held moveably in its associated holder (3), wherein each insert (2) is sealed in the holder (3) by means of a sealing, wherein each insert (2) is moveable within the holder (3) in order to rupture the sealing before the formulation is forced out of the cylinder (4) through the atomizing means (7) in order to generate the spray (13) of the formulation.

2. Inhaler according to claim 1, characterized in that the inhaler (16) comprises a means to pressurize the liquid (5) and force it out through the atomizing means (7), said means comprising a push rod (12), to push or propel the respective piston (6) towards the atomizing means (7).

3. Inhaler according to claim 2, characterized in that the means to push or propel the piston (6) comprises a gas spring (14).

4. Inhaler according to claim 2, characterized in that the means to push or propel the piston (6) comprises a gas spring (14) for driving the push rod (12).

* * * * *

UNITED STATES PATENT AND TRADEMARK OFFICE
CERTIFICATE OF CORRECTION

PATENT NO. : 8,714,151 B2 Page 1 of 1
APPLICATION NO. : 12/812624
DATED : May 6, 2014
INVENTOR(S) : Stephen T. Dunne It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 545 days.

Signed and Sealed this

Twenty-ninth Day of September, 2015

Michelle K. Lee
*Director of the United States Patent and Trademark Office*